(12) United States Patent
Lee

(10) Patent No.: US 12,006,315 B2
(45) Date of Patent: Jun. 11, 2024

(54) INTERMEDIATE USEFUL FOR THE SYNTHESIS OF TGF-BETA INHIBITORS AND A METHOD OF PREPARING TGF-BETA INHIBITORS USING THE SAME

(71) Applicant: MEDPACTO INC., Seoul (KR)

(72) Inventor: Seung Ho Lee, Seoul (KR)

(73) Assignee: MEDPACTO INC., Seoul (KR)

( * ) Notice: Subject to any disclaimer, the term of this patent is extended or adjusted under 35 U.S.C. 154(b) by 0 days.

(21) Appl. No.: 18/188,912

(22) Filed: Mar. 23, 2023

(65) Prior Publication Data

US 2023/0303568 A1    Sep. 28, 2023

(30) Foreign Application Priority Data

Mar. 25, 2022 (KR) .................. 10-2022-0037241

(51) Int. Cl.
*C07D 471/04* (2006.01)
(52) U.S. Cl.
CPC .................. *C07D 471/04* (2013.01)
(58) Field of Classification Search
CPC .................................................. C07D 471/04
See application file for complete search history.

(56) References Cited

U.S. PATENT DOCUMENTS 8,080,568 B1 * 12/2011 Kim .................. A61P 9/08
514/357

FOREIGN PATENT DOCUMENTS

| JP | 2007-000051 A | 1/2007 |
|----|---------------|--------|
| KR | 10-1500665 B1 | 3/2015 |
| KR | 10-2016-0056489 A | 5/2016 |

OTHER PUBLICATIONS

Krishnaiah et al. Synthesis and biological evaluation of 2-benzylamino-4(5)-(6-methylpyridin-2-yl)-5(4)-([1,2,4]triazolo[1,5-α]-pyridin-6-yl)thiazoles as transforming growth factor-β type 1 receptor kinase inhibitors. Eur. J. Med. Chem., 57 (2012), pp. 74-84. (Year: 2012).*
Yang et al., "Hydrolysis of soybean isoflavone glycosides by a thermostable β-glucosidase from Paecilomyces thermophile," Food Chemistry, vol. 115, Issue 4, Sep. 8, 2009; pp. 1247-1252.

* cited by examiner

*Primary Examiner* — Matthew P Coughlin
*Assistant Examiner* — Ashli Ariana Chicks
(74) *Attorney, Agent, or Firm* — Sterne, Kessler, Goldstein & Fox P.L.L.C.

(57) ABSTRACT

The present invention provides an intermediate for synthesizing a TGF-β inhibitor represented by Chemical Formula 1 and an improved method for preparing the TGF-β inhibitor represented by Chemical Formula 1 using the same. The preparation method according to the present invention can not only allow inexpensive and safe reagents to be used, but also simplify the synthesis steps and purification methods to improve the reaction yield, thereby maximizing the production efficiency of the TGF-β inhibitor represented by Chemical Formula 1 to be used usefully for mass production.

19 Claims, No Drawings

INTERMEDIATE USEFUL FOR THE SYNTHESIS OF TGF-BETA INHIBITORS AND A METHOD OF PREPARING TGF-BETA INHIBITORS USING THE SAME

CROSS-REFERENCE TO RELATED APPLICATION

This application claims priority to and the benefit of Korean Patent Application No. 2022-0037241, filed on 25 Mar. 2022, the disclosure of which is incorporated herein by reference in its entirety.

BACKGROUND

1. Field of the Invention

The present invention relates to an intermediate useful for the synthesis of a TGF-β inhibitor and a method of preparing a TGF-β inhibitor.

2. Discussion of Related Art

Transforming growth factor (TGF)-β is a cytokine that regulates cell proliferation and differentiation, wound healing, extracellular matrix production, and the like. The TGF-β family belongs to the TGF-β superfamily, and the TGF-β superfamily includes activin, inhibin, bone morphogenetic proteins, and an anti-Mullerian hormone. Tumor and stromal cells in late-stage tumors of various cancers generally overexpress TGF-β. TGF-β may cause angiogenesis, stimulation of cell migration, inhibition of the immune system, and increased interaction of tumor cells with the extracellular matrix. TGF-β receptors are serine/threonine kinase receptors, and are divided into TGF-β receptor 1, TGF-β receptor 2, and TGF-β receptor 3. Among them, TGF-β receptor 1 is also called activin A receptor type II-like kinase (ALK5).

Regarding TGF-β inhibitors, Korean Patent No. 10-1500665 (Patent Document 1) provides a compound represented by the following Chemical Formula 1, which exhibits excellent TGF-β signaling pathway inhibitory activity by disclosing 2-pyridyl-substituted imidazoles as therapeutic ALK5 and/or ALK4 inhibitors, or a pharmaceutically acceptable salt thereof, and a method for preparing the same.

[Chemical Formula 1]

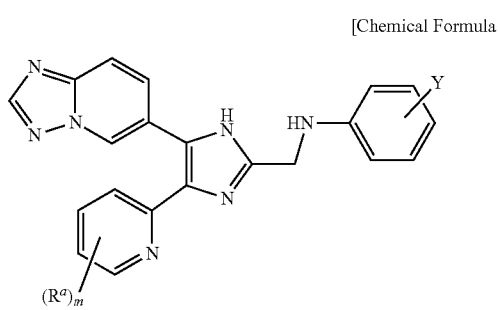

Korean Patent No. 10-1500665 discloses a method for preparing 2-pyridyl-substituted imidazole (I) represented by Chemical Formula 1 above, the method including: preparing an N,P-acetal compound (III) by reacting a pyridine-2-carbaldehyde compound (II) with aniline and diphenyl phosphite as shown in the following Reaction Scheme A; combining the N,P-acetal compound (III) with [1,2,4]triazolo[1,5-a]pyridine-6-carbaldehyde and then preparing a monoketone compound (IV) under acidic conditions; preparing a diketone compound (V) by oxidizing the monoketone compound (IV); preparing an acetal-protected imidazole compound (VI) by condensing the diketone compound (V) with 2,2-dimethoxyacetaldehyde; preparing an imidazole-2-carbaldehyde compound (VII) by hydrolyzing the acetal-protected imidazole compound (VI) under acidic conditions; and combining the imidazole-2-carbaldehyde compound (VII) with an aniline compound (VIII) under acidic conditions to produce an imine compound and reducing the imine compound.

[Reaction Scheme A]

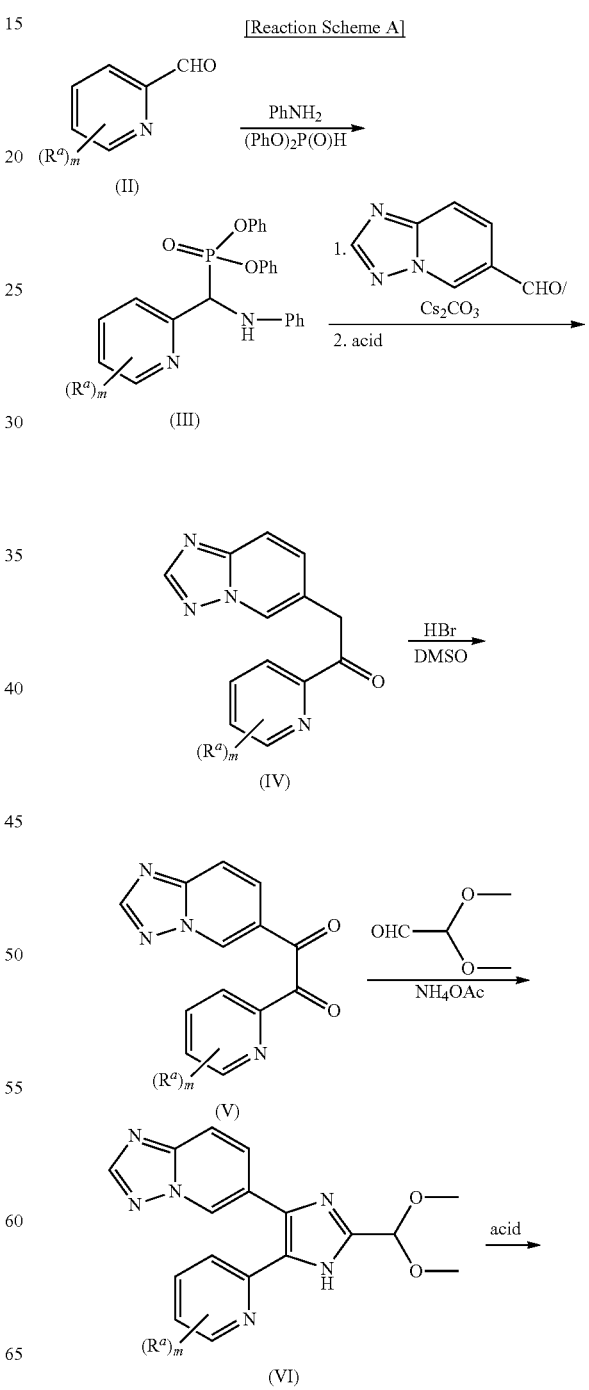

-continued

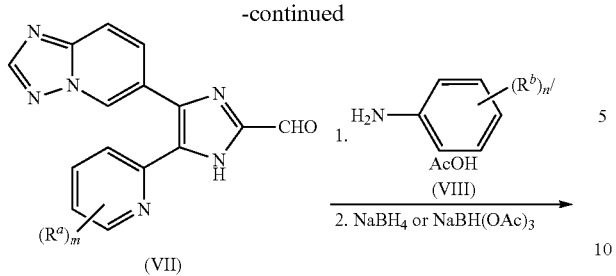

(VII)

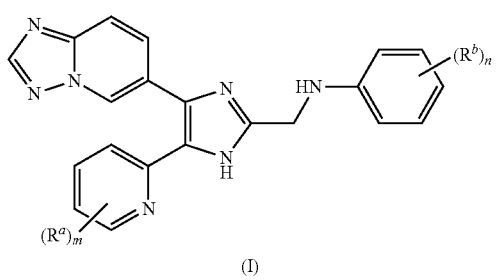

(I)

However, since the method prepares the compound through a long process, the reaction yield is low, the reaction needs to be carried out for a long time, and expensive reagents and complicated purification processes are required, so that there is a disadvantage in that the method is not suitable for commercial mass production.

Therefore, the present inventors have identified a preparation method suitable for mass production, which is not only economically feasible using inexpensive and low-toxic and low-hazardous reagents, but also can prepare a final compound with an improved yield by reducing the reaction steps, thereby completing the present invention.

RELATED ART DOCUMENTS

Patent Documents (Patent 0001) Korean Patent No. 10-1500665

SUMMARY OF THE INVENTION

The present invention is intended to provide a novel method for preparing a compound of Chemical Formula 2, a compound of Chemical Formula 4 and a compound of Chemical Formula 5, which are intermediates useful for the synthesis of TGF-β inhibitors.

The present inventors developed a synthesis method with short reaction steps and a high total yield by utilizing more commercially available starting materials in synthesizing the compound of the following Chemical Formula 1, thereby completing the present invention.

The compound of Chemical Formula I, which is a final target compound and an active ingredient used as a TGF-β inhibitor, is as follows.

[Chemical Formula 1]

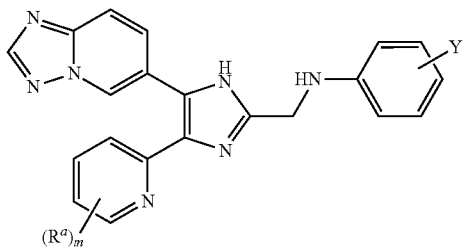

In the formula,

X is halogen (for example, F, Cl, Br or I);

$R^a$ is independently hydrogen, halogen, C1-6 alkyl, C1-6 haloalkyl, C3-6 cycloalkyl, hydroxyl, —O—C1-6 alkyl, —O—C1-6 haloalkyl, —O—C3-6 cycloalkyl, amino, —NH—C1-6 alkyl, —NH—C1-6 haloalkyl, —NH—C3-6 cycloalkyl, —S—C1-6 alkyl, —S—C1-6 haloalkyl, —S—C3-6 cycloalkyl, cyano, or nitro; and m is 0, 1, 2, 3 or 4.

For example, the compound of Chemical Formula 1 may be a compound of the following Chemical Formula 1a.

[Chemical Formula 1a]

The present invention provides a method for preparing the compound of Chemical Formula 1, the method including the following steps.

obtaining a compound of Chemical Formula 4 by reacting a compound of Chemical Formula 2 with a compound of Chemical Formula 3, and obtaining a compound of Chemical Formula 1 by deprotecting the compound of Chemical Formula 4.

[Chemical Formula 2]

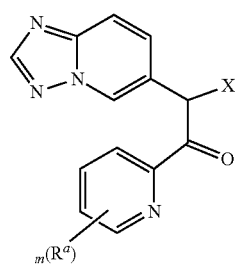

[Chemical Formula 3]

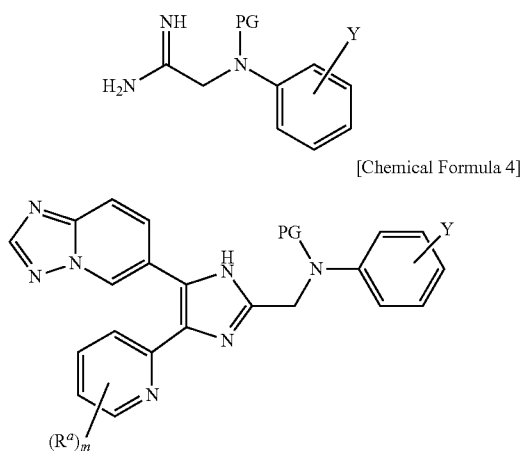

[Chemical Formula 4]

In the formulae,

X and Y are each independently halogen (for example, F, Cl, Br or I);

PG is a protecting group selected from the group consisting of butoxycarbonyl (Boc), benzyloxycarbonyl (Cbz), 9-fluorenylmethoxycarbonyl (Fmoc), acetyl, benzoyl and tosyl;

in this case, $R^a$ is independently hydrogen, halogen, C1-6 alkyl, C1-6 haloalkyl, C3-6 cycloalkyl, hydroxyl, —O—C1-6 alkyl, —O—C1-6 haloalkyl, —O—C3-6 cycloalkyl, amino, —NH—C1-6 alkyl, —NH—C1-6 haloalkyl, —NH—C3-6 cycloalkyl, —S—C1-6 alkyl, —S—C1-6 haloalkyl, —S—C3-6 cycloalkyl, cyano, or nitro; and m is 0, 1, 2, 3 or 4.

For example, the compound of Chemical Formula 2 may be a compound of the following Chemical Formula 2a.

[Chemical Formula 2a]

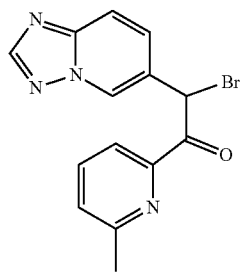

For example, the compound of Chemical Formula 3 may be a compound of the following Chemical Formula 3a.

[Chemical Formula 2a]

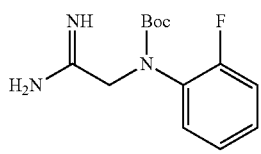

For example, the compound of Chemical Formula 4 may be a compound of the following Chemical Formula 4a.

[Chemical Formula 4a]

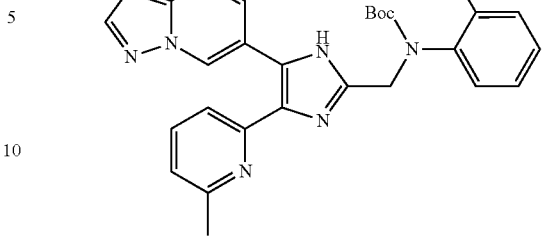

In Korean Patent No. 10-1500665 (Patent Document 1), a process for preparing a compound of Chemical Formula 1 consists of a total of 6 steps (Reaction Scheme A). Further, a reaction may be performed using dibenzyl phosphate and [1,2,4]triazolo[1,5-a]pyridine-6-carbaldehyde when the reaction is performed using II as a starting material, and in this case, not only the cost of purchasing reagents is high, but also 3 out of 6 steps require a purification process using column chromatography, making it difficult to apply the process to mass production.

To solve such problems in the related art, in an exemplary embodiment of the present invention, commercially available 2-fluoroaniline (a compound of the following Chemical Formula 8), 2-(2-fluorophenylamino)acetonitrile (a compound of the following Chemical Formula 7), tert-butyl cyanomethyl(2-fluorophenyl)carbamate (a compound of the following Chemical Formula 6), or tert-butyl 2-amino-2-iminoethyl(2-fluorophenyl)carbamate (a compound of the following Chemical Formula 3) (including a salt form) may be used as a starting material for obtaining a compound of Chemical Formula 1.

In an exemplary embodiment of the present invention, through a process of forming imidazole by introducing a Boc-protecting group using 2-fluoroaniline (a compound of the following Chemical Formula 8) as a starting material, a compound of Chemical Formula 1 may be subjected to a purification process by a simple washing method except for only one column chromatography step compared to a method of performing three steps of column chromatography purification in the existing method according to Korean Patent No. 10-1500665 (Patent Document 1) by an efficient process having a total of 5 steps, and production efficiency may be maximized by reducing the number of synthesis steps to a total of 5 steps. In addition, the compound can be produced even in mass production, and economic feasibility can also be greatly improved as the compound can be produced with high yield.

In an exemplary embodiment, since the method for preparing a compound of Chemical Formula 1 according to the present invention may prepare the compound of Chemical Formula 1 by including the following Steps 1 to 5 and a compound of Chemical Formula 8, a compound of Chemical Formula 7, a compound of Chemical Formula 6, or a compound of Chemical Formula 3 may be selected as a starting material, one or more of Steps 1 to 3 may not be required, if necessary.

obtaining a compound of Chemical Formula 7 from a compound of Chemical Formula 8 (Step 1), obtaining a compound of Chemical Formula 6 from the compound of Chemical Formula 7 (Step 2), obtaining a compound of Chemical Formula 3 from the compound of Chemical Formula 6 (Step 3), obtaining a compound of Chemical Formula 4 by reacting the compound of Chemical Formula 3 with a compound of Chemical Formula 2 (Step 4), and obtaining a compound of Chemical Formula 1 from the compound of Chemical Formula 4 (Step 5).

[Chemical Formula 8]

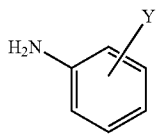

[Chemical Formula 7]

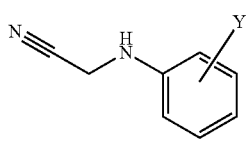

[Chemical Formula 6]

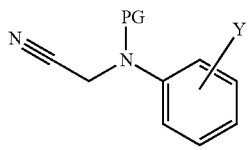

In the formulae, Y is halogen; and

PG is a protecting group selected from the group consisting of butoxycarbonyl (Boc), benzyloxycarbonyl (Cbz), 9-fluorenylmethoxycarbonyl (Fmoc), acetyl, benzoyl and tosyl.

The obtaining of the compound of Chemical Formula 7 from the compound of Chemical Formula 8 (Step 1) may include obtaining the compound of Chemical Formula 3 by introducing acetonitrile into the amine of the compound of Chemical Formula 8 in the presence of a base.

The base may be selected from the group consisting of sodium hydrogen carbonate, sodium carbonate, and potassium carbonate.

Step 1 may be performed at 70° C. to 90° C. to maximize the yield.

The obtaining of the compound of Chemical Formula 6 from the compound of Chemical Formula 7 (Step 2) may include obtaining the compound of Chemical Formula 6 by introducing an amine protecting group into the compound of Chemical Formula 7.

The amine protecting group may be selected from the group consisting of butoxycarbonyl (Boc), benzyloxycarbonyl (Cbz), 9-fluorenylmethoxycarbonyl (Fmoc), acetyl, benzoyl and tosyl.

The obtaining of the compound of Chemical Formula 3 from the compound of Chemical Formula 6 (Step 3) may include obtaining a compound of the following Chemical Formula 6' by converting the nitrile of the compound of Chemical Formula 6 into acetimidate, and obtaining a compound of Chemical Formula 3 converted into an amidine by reacting the compound of Chemical Formula 6' with ammonia.

[Chemical Formula 6']

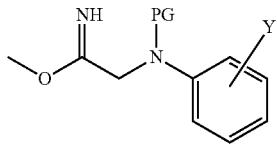

In the formula, Y is halogen; and

PG is a protecting group selected from the group consisting of butoxycarbonyl (Boc), benzyloxycarbonyl (Cbz), 9-fluorenylmethoxycarbonyl (Fmoc), acetyl, benzoyl and tosyl.

Step 3 may include Step 3-1 of obtaining a compound of the following Chemical Formula 6' by converting the nitrile of the compound of Chemical Formula 6 into acetimidate, and Step 3-2 of obtaining a compound of Chemical Formula 3 converted into an amidine by reacting the compound of Chemical Formula 6' with ammonia.

It may be advantageous to use preferably methanol as a solvent used in the obtaining of the compound of Chemical Formula 6' from the compound of Chemical Formula 6 (Step 3-1) and the obtaining of the compound of Chemical Formula 3 from the compound of Chemical Formula 6' (Step 3-2) in consideration of the reaction temperature and the ease of subsequent concentration removal of the solvent.

The obtaining of the compound of Chemical Formula 6' from the compound of Chemical Formula 6 and the obtaining of the compound of Chemical Formula 3 from the compound of Chemical Formula 6' may be performed at 20° C. to 50° C., but the temperature is not limited thereto. The preferred reaction temperature may be set to a temperature at which the solvent can be refluxed depending on the choice of solvent.

It is preferred to perform Step 3-1 for a reaction time of 36 to 60 hours, for example, 36 to 48 hours, and when the reaction time is out of the above range, there may be a problem in that the reaction is not sufficiently carried out, or an addition reaction occurs, resulting in a decrease in yield.

It is preferred to perform Step 3-2 for a reaction time of 2 to 96 hours, and when the reaction time is out of the above range, there is a problem in that the reaction is not sufficiently carried out, or an addition reaction occurs, resulting in a decrease in yield.

The ammonia may be selected from the group consisting of a methanolic ammonia solution, ammonium chloride and ammonium bicarbonate.

When the methanolic ammonia solution is used, a metal salt may be further included as a catalyst to shorten the reaction time.

In Step 3, after Step 3-1 is completed, Step 3-2 may be performed without a separate post-treatment or purification process.

In an exemplary embodiment of the present invention, the obtaining of the compound of Chemical Formula 6' from the compound of Chemical Formula 6 and the obtaining of the compound of Chemical Formula 3 from the compound of Chemical Formula 6' may be performed in methanol, and may be performed at a reaction temperature of 1° C. to 35° C.

A process of synthesizing the compound of Chemical Formula 6' from the compound of Chemical Formula 6 using methanol and again synthesizing a hydrochloride of the compound of Chemical Formula 3 from the compound of Chemical Formula 6' using ammonium chloride is exemplarily represented by the following reaction scheme.

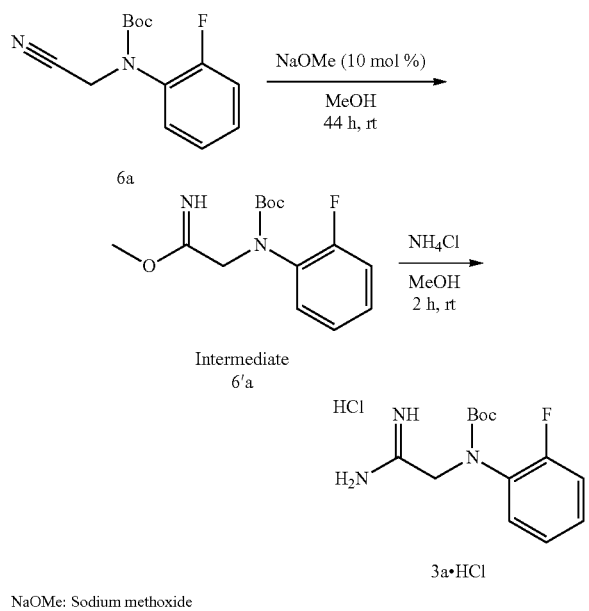

NaOMe: Sodium methoxide
MeOH: Methanol
NH₄Cl: Ammonium chloride

In Step 3-2 of obtaining the compound of Chemical Formula 3 from the compound of Chemical Formula 6', the compound of Chemical Formula 3 is obtained by reacting the compound of Chemical Formula 6' with ammonium chloride. In this case, the compound of Chemical Formula 3 may be obtained with high purity by forming a hydrochloride.

The obtaining of the compound of Chemical Formula 4 by reacting the compound of Chemical Formula 3 with the compound of Chemical Formula 2 (Step 4) may include obtaining a compound of the following Chemical Formula 2' by substituting the halogen of the compound of Chemical Formula 3 with an amine of the compound of Chemical Formula 2 in the presence of a base, and obtaining a compound of Chemical Formula 4 by forming imidazole by a dehydration reaction between the amine and carbonyl of the compound of Chemical Formula 2'.

[Chemical Formula 2']

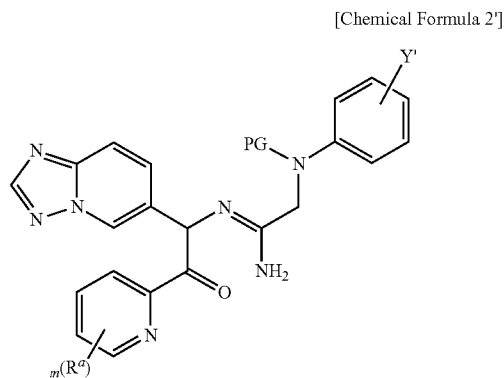

Y is halogen;
PG is a protecting group selected from the group consisting of butoxycarbonyl (Boc), benzyloxycarbonyl (Cbz), 9-fluorenylmethoxycarbonyl (Fmoc), acetyl, benzoyl and tosyl;
$R^a$ is independently hydrogen, halogen, C1-6 alkyl, C1-6 haloalkyl, C3-6 cycloalkyl, hydroxyl, —O—C1-6 alkyl, —O—C1-6 haloalkyl, —O—C3-6 cycloalkyl, amino, —NH—C1-6 alkyl, —NH—C1-6 haloalkyl, —NH—C3-6 cycloalkyl, —S—C1-6 alkyl, —S—C1-6 haloalkyl, —S—C3-6 cycloalkyl, cyano, or nitro; and
m is 0, 1, 2, 3 or 4.

Step 4 may include Step 4-1 of obtaining a compound of the following Chemical Formula 2' by substituting the halogen of the compound of Chemical Formula 3 with an amine of the compound of Chemical Formula 2, and Step 4-2 of obtaining the compound of Chemical Formula 4 by forming imidazole by a dehydration reaction between the amine and carbonyl of the compound of Chemical Formula 2'.

In Step 4, it is possible to use dimethylformamide (N,N-dimethylformamide, DMF), acetonitrile, tetrahydrofuran (THF), toluene or a mixture thereof as a reaction solvent.

The reaction of Step 4 may be performed at 20° C. to 95° C., for example, 30° C. to 80° C., 30° C. to 70° C., and 40° C. to 60° C. In order to minimize the production of related materials and reaction intermediates, the reaction may be preferably performed at 30° C. to 60° C.

The base may be selected from the group consisting of potassium bicarbonate, potassium carbonate, potassium phosphate, sodium acetate, 1,4-diazabicyclo[2.2.2]octane (DABCO), and triethylamine.

The base may be used in an amount of 3 to 5 equivalents, preferably 3 to 4 equivalents, relative to 1 equivalent of the compound of Chemical Formula 3, but the amount is not limited thereto.

The reaction further includes a desiccant to prevent side reactions, and as the desiccant, those selected from among molecular sieves, sodium sulfate and magnesium sulfate may be used.

Step 4 may be performed for a reaction time of 3 to 36 hours, and preferably for 24 to 36 hours in order to minimize the production of related materials and reaction intermediates.

In an exemplary embodiment of the present invention, the obtaining of the compound of Chemical Formula 2' from the compound of Chemical Formula 3 and the obtaining of the compound of Chemical Formula 4 from the compound of Chemical Formula 2' may be performed at 20° C. to 95° C., but the temperature is not limited thereto. The preferred reaction temperature may be set to a temperature at which the solvent can be refluxed depending on the choice of solvent. In an exemplary embodiment of the present invention, the obtaining of the compound of Chemical Formula 2' from the compound of Chemical Formula 3 and the obtaining of the compound of Chemical Formula 4 from the compound of Chemical Formula 2' may be performed in acetonitrile, and may be performed at 30° C. to 60° C.

The process of synthesizing the compound of Chemical Formula 2' using acetonitrile and again synthesizing the compound of Chemical Formula 4 from the compound of Chemical Formula 2' is exemplarily represented by the following reaction scheme.

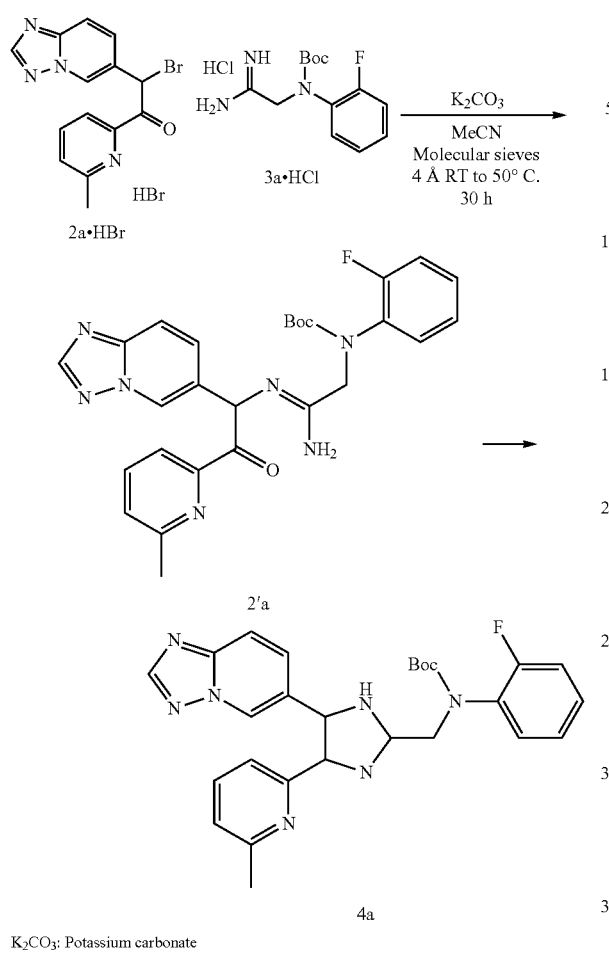

K₂CO₃: Potassium carbonate
MeCN: Acetonitrile

The solubility of the reactants may be increased for ease of mass production using acetonitrile as a reaction solvent. Furthermore, reaction efficiency may be improved using a molecular sieve as a desiccant.

The obtaining of the compound of Chemical Formula 1 from the compound of Chemical Formula 4 (Step 5) may include obtaining the compound of Chemical Formula 1 by deprotecting the compound of Chemical Formula 4.

An amine protecting group is removed by reacting the compound of Chemical Formula 4 under acidic conditions, and for the removal of a protecting group, when the amine protecting group is butoxycarbonyl (Boc), the protecting group may be removed by a reaction under acidic conditions such as trifluoroacetic acid/dichloromethane, ethyl acetate/hydrogen chloride, diethylacetate/hydrogen chloride, hydrogen chloride/dichloromethane or methanol/hydrogen chloride, and when the amine protecting group is benzyloxycarbonyl (Cbz), the protecting group may be removed through a hydrogen reaction in the presence of palladium/carbon.

In Step 5, dichloromethane, ethylacetate, methanol or a mixture thereof may be used as a reaction solvent.

The acid may be used in an amount of 8 to 12 equivalents, preferably 9 to 11 equivalents, relative to 1 equivalent of the compound of Chemical Formula 4, but the amount is not limited thereto.

In another exemplary embodiment of the present invention, the compound of Chemical Formula 2 may be prepared by a method including obtaining the compound of Chemical Formula 2 from the compound of Chemical Formula 5, and the method may include obtaining the compound of Chemical Formula 2 from a compound of the following Chemical Formula 5 (Step A).

[Chemical Formula 5]

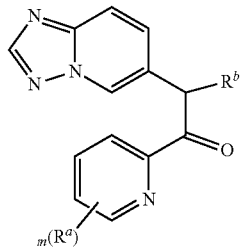

In the formula, $R^a$ is independently hydrogen, halogen, C1-6 alkyl, C1-6 haloalkyl, C3-6 cycloalkyl, hydroxyl, —O—C1-6 alkyl, —O—C1-6 haloalkyl, —O—C3-6 cycloalkyl, amino, —NH—C1-6 alkyl, —NH—C1-6 haloalkyl, —NH—C3-6 cycloalkyl, —S—C1-6 alkyl, —S—C1-6 haloalkyl, —S—C3-6 cycloalkyl, cyano, or nitro; and m is 0, 1, 2, 3 or 4;

$R^b$ is hydrogen, hydroxyl, cyano, nitro, or amino.

The obtaining of the compound of Chemical Formula 2 from the compound of Chemical Formula 5 (Step A) may include obtaining the compound of Chemical Formula 2 by converting an $R^b$ substituent of the compound of Chemical Formula 5 into a halogen using a halogenating reagent.

In Step A, acetic acid, dioxane or a mixture thereof may be used as a reaction solvent.

When $R^b$ is hydrogen, preferably, acetic acid may be used to form a salt, thereby effectively removing impurities generated during the reaction and obtaining the compound of Chemical Formula 2 with high purity.

In Step A, reactants may be washed with a solvent to remove impurities, and preferably, it is possible to additionally include a process of washing with MTBE.

The present invention also provides a compound of Chemical Formula 2 or a salt thereof, which is a useful intermediate for the synthesis of a compound of Chemical Formula 1.

[Chemical Formula 2]

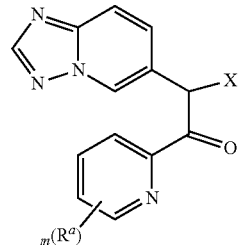

In the formula,

X is halogen;

$R^a$ is independently hydrogen, halogen, C1-6 alkyl, C1-6 haloalkyl, C3-6 cycloalkyl, hydroxyl, —O—C1-6 alkyl, —O—C1-6 haloalkyl, —O—C3-6 cycloalkyl, amino, —NH—C1-6 alkyl, —NH—C1-6 haloalkyl, —NH—C3-6 cycloalkyl, —S—C1-6 alkyl, —S—C1-6 haloalkyl, —S—C3-6 cycloalkyl, cyano, or nitro; and m is 0, 1, 2, 3 or 4.

In an exemplary embodiment of the present invention, the compound of Chemical Formula 2 may be a compound of Chemical Formula 2a.

[Chemcial Formula 2a]

Although not limited thereto, the salt of the compound of Chemical Formula 2 may be a hydrofluoric acid (HF), hydrobromic acid (HBr), hydrochloric acid (HCl), or hydroiodic acid (HI). The present invention also provides a compound of Chemical Formula 4 or a salt thereof, which is a useful intermediate for the synthesis of a compound of Chemical Formula 1.

[Chemical Formula 4]

In the formula,

PG is a protecting group selected from the group consisting of butoxycarbonyl (Boc), benzyloxycarbonyl (Cbz), 9-fluorenylmethoxycarbonyl (Fmoc), acetyl, benzoyl and tosyl;

Y is halogen;

$R^a$ is independently hydrogen, halogen, C1-6 alkyl, C1-6 haloalkyl, C3-6 cycloalkyl, hydroxyl, —O—C1-6 alkyl, —O—C1-6 haloalkyl, —O—C3-6 cycloalkyl, amino, —NH—C1-6 alkyl, —NH—C1-6 haloalkyl, —NH—C3-6 cycloalkyl, —S—C1-6 alkyl, —S—C1-6 haloalkyl, —S—C3-6 cycloalkyl, cyano, or nitro; and m is 0, 1, 2, 3 or 4.

In an exemplary embodiment of the present invention, the compound of Chemical Formula 4 may be a compound of Chemical Formula 4a.

[Chemical Formula 4a]

Although not limited thereto, the salt of the compound of Chemical Formula 4 may be a hydrofluoric acid (HF), hydrobromic acid (HBr), hydrochloric acid (HCl), or hydroiodic acid (HI).

DETAILED DESCRIPTION OF EXEMPLARY EMBODIMENTS

Hereinafter, the present invention will be described in more detail by examples. However, the following examples are only for exemplifying the present invention, and the scope of the present invention is not limited to these examples.

Abbreviations

The meanings of the abbreviations described in the following examples are as follows.
AcOH: Acetic acid
$Boc_2O$: Di-tert-butyl dicarbonate
$Br_2$: Bromine
2-butanone: 2-Butanone
chloroacetonitrile: Chloroacetonitrile
$CH_2Cl_2$: Dichloromethane
DABCO: 1,4-Diazabicyclo[2.2.2]octane
DMAP: 4-Dimethylaminopyridine
DMF: N,N-Dimethylformamide
$Et_3N$: Triethylamine
EtOH: Ethanol
EtOAc: Ethyl acetate
HBr: Hydrobromide
HCl: Hydrochloride
$K_2CO_3$: Potassium carbonate
$KHCO_3$: Potassium hydrogen carbonate
$K_3PO_4$: Tripotassium phosphate
MeOH: Methanol
MeCN: Acetonitrile
$MgSO_4$: Magnesium sulfate
MS: Molecular sieves
MTBE: Methyl tertiary butyl ether
$NaHCO_3$: Sodium hydrogen carbonate
NaI Sodium iodide
NaOAc: Sodium acetate
NaOMe: Sodium methoxide
$NH_4Cl$: Ammonium chloride
$NH_4HCO_3$: Ammonium bicarbonate
THF: Tetrahydrofuran
toluene: Toluene
$Zn(OTf)_2$: Zinc trifluoromethanesulfonate In the following, Example 1 exemplifies the process of synthesizing the compound of Chemical Formula 1a, which is a preferred example of the compound of Chemical Formula 1, and Example 2 exemplifies the process of synthesizing the compound of Chemical Formula 2a, which is a preferred example of the compound of Chemical Formula 2.

The following Reaction Scheme 1 schematically illustrates the process of synthesizing the compound of Chemical Formula 1a.

[Reaction Scheme 1]

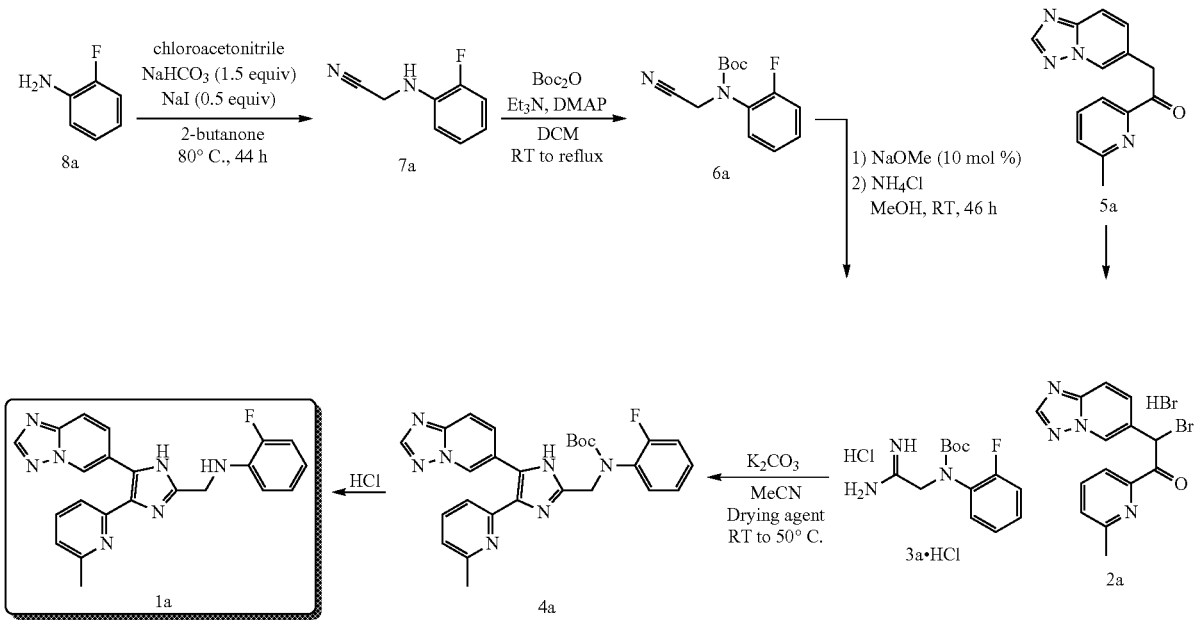

EXAMPLES

Example 1: Preparation of N-((5-([1,2,4]triazolo[1,5-a]pyridin-6-yl)-4-(6-methylpyridin-2-yl)-1H-imidazol-2-yl)methyl)-2-fluoroaniline (Compound 1a)

Step 1: Preparation of 2-(2-fluorophenylamino)acetonitrile (Compound 7a)

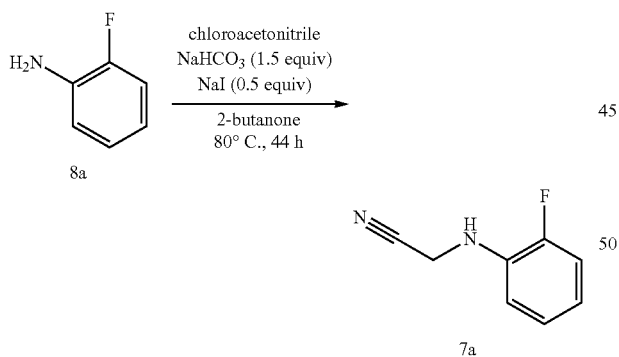

After 2-fluoroaniline (1 equivalent) and chloroacetonitrile (1 equivalent) were put into 2-butanone and the resulting mixture was stirred, sodium hydrogen carbonate (1.5 equivalents) and sodium iodide (0.5 equivalent) were added thereto, and the resulting mixture was refluxed. After the reaction was completed, the resulting product was cooled to room temperature, and then the solvent was removed under reduced pressure. The solvent-free mixture was washed with methylbutyl ether and dried to obtain 50 g of a target compound 2-(2-fluorophenylamino)acetonitrile in a yield of 95%.

Step 2: Preparation of tert-butyl cyanomethyl(2-fluorophenyl)carbamate (Compound 6a)

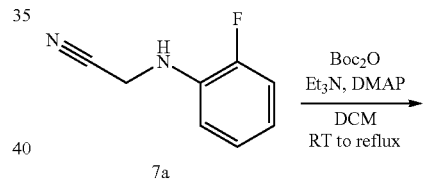

After 2-(2-fluorophenylamino)acetonitrile was put into dichloromethane and the resulting mixture was stirred, triethylamine, di-tert-butyl dicarbonate, and 4-dimethylaminopyridine were added thereto, and the resulting mixture was refluxed. After the reaction was completed, the resulting product was cooled to room temperature, and then the solvent was removed under reduced pressure. The solvent-free mixture was subjected to column chromatography (silica, ethyl acetate/heptane) to remove residual 4-dimethylaminopyridine and obtain 5 g of a target product tert-butyl cyanomethyl(2-fluorophenyl)carbamate in a yield of 76%.

Step 3: Preparation of tert-butyl 2-amino-2-iminoethyl(2-fluorophenyl)carbamate hydrochloride (Compound 3a)

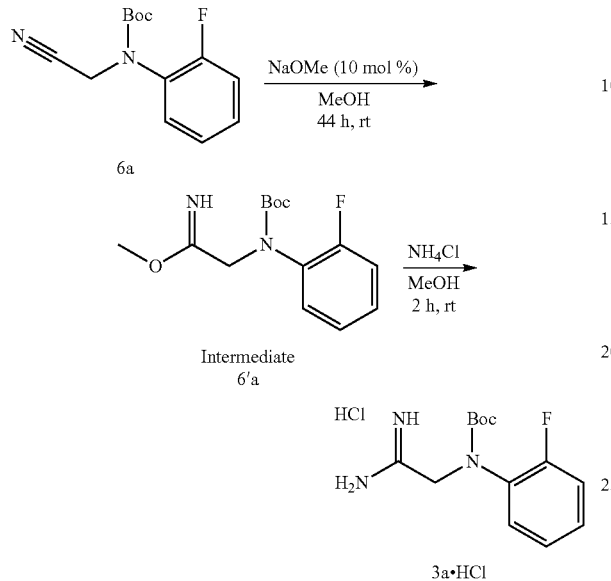

NH₃ in MeOH(7N)+cat. Zn(OTf)₂/NH₄Cl/NH₄HCO₃ was applicable as the ammonia reagent used in the synthesis of Compound 3a.

TABLE 1

| Type of ammonia | Equivalent | Reaction time | Compound 77 | Purity |
|---|---|---|---|---|
| NH₃ in MeOH(7N) + cat. Zn(OTf)₂ | 5 | Day 4 | 115% | 65% |
| NH₄Cl | 1 | 2 h | 80% | >99% |
| NH₄HCO₃ | 1 | 2 h | 105% | 73% |

NH₄Cl (ammonium chloride) was selected in consideration of reaction time and ease of subsequent purification.

Preferred synthesis examples according to the above results are as follows.

After tert-butyl cyanomethyl(2-fluorophenyl)carbamate (3.25 g, 13.0 mmol) was dissolved in anhydrous methanol, a sodium methoxide solution (5.4 M in MeOH, 0.24 ml, 1.30 mmol) was added thereto and the resulting mixture was reacted for 44 hours. When the reaction was completed, ammonium chloride (0.695 g, 12.99 mmol) was added thereto and the resulting mixture was reacted at room temperature for 2 hours. After the reaction was completed, the solvent was removed under reduced pressure. The solvent-free mixture was washed with methyl butyl ether and dried to obtain 3.3 g of a target compound tert-butyl 2-amino-2-iminoethyl(2-fluorophenyl)carbamate hydrochloride in a yield of 92%.

Step 4: Preparation of tert-butyl (5-([1,2,4]triazolo[1,5-a]pyridin-6-yl)-4-(6-methylpyridin-2-yl)-1H-imidazol-2-yl)methyl(2-fluorophenyl)carbamate (Compound 4a)

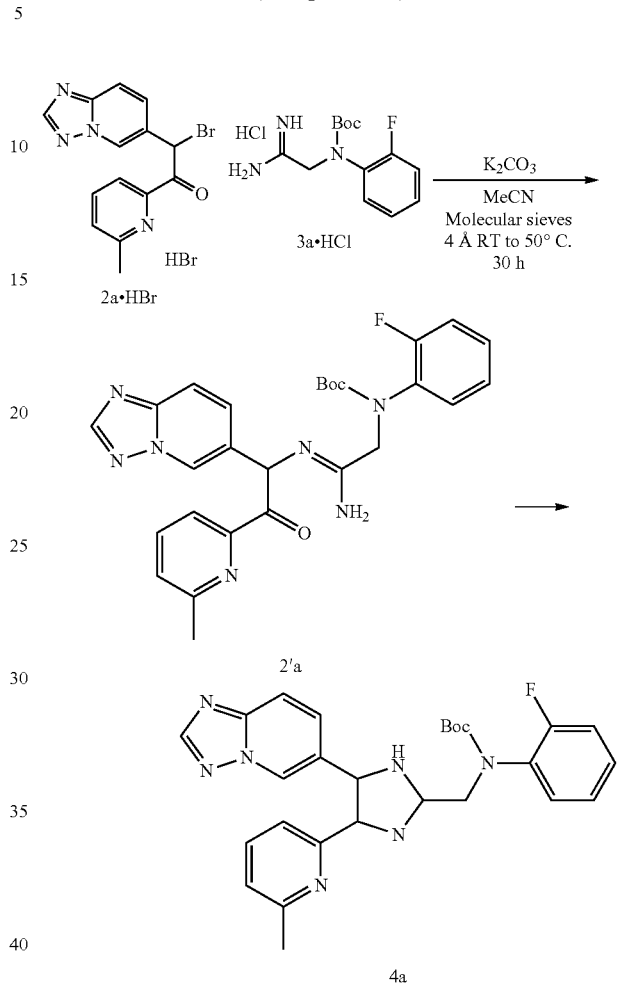

K₂CO₃/KHCO₃/K₃PO₄/NaOAc/DABCO/Et₃N was applicable as the base used in the synthesis of Compound 4a.

TABLE 2

| Type of solvent | Type of base | Reaction temperature (° C.) | Reaction time (h) | Compound 4a | Compound 2'a (Intermediate) |
|---|---|---|---|---|---|
| DMF | K₂CO₃ | 30 | 3 | 42.5% | 27.3% |
| DMF | KHCO₃ | 30 | 3 | 22.8% | 23.4% |
| DMF | K₃PO₄ | 30 | 3 | 29.5% | 31.5% |
| DMF | NaOAc | 30 | 3 | 0.0% | 1.7% |
| DMF | DABCO | 30 | 3 | 0.0% | 0.2% |
| DMF | Et₃N | 30 | 3 | Mixture | |
| DMF | K₂CO₃ | 30 | 24 | 70.6% | 1.3% |
| DMF | KHCO₃ | 30 | 24 | 58.8% | 1.7% |
| DMF | K₃PO₄ | 30 | 24 | 65.1% | 1.1% |
| DMF | NaOAc | 30 | 24 | 0.3% | 0.3% |
| DMF | DABCO | 30 | 24 | 0.0% | 0.0% |
| DMF | Et₃N | 30 | 24 | N.D. | N.D. |
| DMF | K₂CO₃ | 50 | 3 | 57.5% | 1.4% |
| DMF | KHCO₃ | 50 | 3 | 42.0% | 2.9% |
| DMF | K₃PO₄ | 50 | 3 | 52.1% | 1.6% |
| DMF | NaOAc | 50 | 3 | 1.0% | 2.4% |
| DMF | DABCO | 50 | 3 | 0.0% | 0.0% |
| DMF | Et₃N | 50 | 3 | Mixture | |

TABLE 2-continued

| Type of solvent | Type of base | Reaction temperature (° C.) | Reaction time (h) | Compound 4a | Compound 2'a (Intermediate) |
|---|---|---|---|---|---|
| DMF | $K_2CO_3$ | 50 | 24 | 57.0% | 1.2% |
| DMF | $KHCO_3$ | 50 | 24 | 42.2% | 1.6% |
| DMF | $K_3PO_4$ | 50 | 24 | 52.9% | 0.0% |
| DMF | NaOAc | 50 | 24 | 1.4% | 0.0% |
| DMF | DABCO | 50 | 24 | 0.0% | 0.0% |
| DMF | $Et_3N$ | 50 | 24 | N.D. | N.D. |

In consideration of the yield, a solvent optimization test was performed after selecting $K_2CO_3$ (potassium carbonate). The reaction solvent was selected from solvents capable of dissolving Compound 3a well and allowing the reaction to proceed in a homogeneous state, and DMF/THF/MeCN/Toluene was applicable as the solvent used.

By confirming that water molecules generated during the reaction participate in the reaction to generate impurities, the yield was improved by further adding a desiccant thereto, and molecular sieves (4 Å)/$MgSO_4$ were applicable as the desiccant.

TABLE 3

| Type of solvent | Type of base | Desiccant | Reaction temperature | Reaction time (h) | Compound 4a | Compound 2'a (Intermediate) | Impurities due to $H_2O$ |
|---|---|---|---|---|---|---|---|
| DMF | $K_2CO_3$ | — | RT | 1 | 14.8% | 73.1% | 0.6% |
| | | | RT | 18 | 68.3% | 24.3% | 2.7% |
| | | | 50° C. | 3 | 87.0% | 1.7% | 4.6% |
| | | $MgSO_4$ | RT | 1 | 5.7% | 79.3% | 0.0% |
| | | | RT | 18 | 63.1% | 27.3% | 0.7% |
| | | | 50° C. | 3 | 90.1% | 2.8% | 2.4% |
| | | MS (4 Å) | RT | 1 | 31.6% | 31.6% | 0.8% |
| | | | RT | 18 | 91.4% | 1.9% | 1.4% |
| | | | 50° C. | 3 | 92.4% | 1.8% | 2.2% |
| THF | $K_2CO_3$ | — | RT | 1 | | Mixture | |
| | | | RT | 18 | | | |
| | | | 50° C. | 3 | | | |
| | | $MgSO_4$ | RT | 1 | 0.0% | 38.8% | 0.0% |
| | | | RT | 18 | 0.2% | 37.8% | 0.0% |
| | | | 50° C. | 3 | 3.0% | 69.7% | 0.3% |
| | | MS (4 Å) | RT | 1 | N.D. | N.D. | N.D. |
| | | | RT | 18 | 68.5% | 26.5% | 1.5% |
| | | | 50° C. | 3 | 68.8% | 28.2% | 1.2% |
| MeCN | $K_2CO_3$ | — | RT | 1 | 13.1% | 58.8% | 1.2% |
| | | | RT | 18 | 21.5% | 74.1% | 0.6% |
| | | | 50° C. | 3 | 53.5% | 40.6% | 1.4% |
| | | $MgSO_4$ | RT | 1 | 6.6% | 66.3% | 0.5% |
| | | | RT | 18 | 30.3% | 63.9% | 0.8% |
| | | | 50° C. | 3 | 59.0% | 36.1% | 2.0% |
| | | MS (4 Å) | RT | 1 | 25.9% | 57.8% | 1.1% |
| | | | RT | 18 | 46.5% | 50.0% | 0.9% |
| | | | 50° C. | 3 | 90.2% | 7.3% | 0.9% |
| Toluene | $K_2CO_3$ | — | RT | 1 | 14.4% | 78.8% | 0.0% |
| | | | RT | 18 | 51.9% | 46.4% | 0.2% |
| | | | 50° C. | 3 | 49.5% | 39.6% | 0.4% |
| | | $MgSO_4$ | RT | 1 | 0.0% | 85.4% | 0.0% |
| | | | RT | 18 | 48.9% | 48.2% | 0.0% |
| | | | 50° C. | 3 | 48.4% | 43.0% | 0.0% |
| | | MS (4 Å) | RT | 1 | 0.0% | 20.7% | 0.0% |
| | | | RT | 18 | 9.7% | 14.3% | 6.8% |
| | | | 50° C. | 3 | | Mixture | |

MS (4 Å): Molecular sieves

Preferred synthesis examples according to the above results are as follows. After tert-butyl 2-amino-2-iminoethyl (2-fluorophenyl)carbamate hydrochloride (81 mg, 0.267 mmol), potassium carbonate (0.134 g, 0.971 mmol), and MS (4 Å)(200 mg) were put into acetonitrile and the resulting mixture was stirred, 2-([1,2,4]triazolo[1,5-a]pyridin-6-yl)-2-bromo-1-(6-methylpyridin-2-yl)ethanone bromate (100 mg, 0.243 m mol) was added thereto at room temperature. The reactants were heated from room temperature to 50° C. and reacted for 30 hours. After the reaction was completed, the solvent was removed from a filtrate obtained by filtration under reduced pressure. The solvent-free mixture was extracted with a saturated aqueous ammonium chloride solution and ethyl acetate. After an organic solvent layer was washed with brine and sodium sulfate, the solvent of the extract was removed under reduced pressure to obtain 98 mg of a target product tert-butyl (5-([1,2,4]triazolo[1,5-a]pyridin-6-yl)-4-(6-methylpyridin-2-yl)-1H-imidazol-2-yl)methyl(2-fluorophenyl)carbamate in a yield of 81%.

$^1$H NMR (CDCl3, 400 MHz) δ10.94 (br s, 1H), 8.93 (br s, 1H), 8.35 (s, 1H), 7.77 (m, 2H), 7.47 (t, 1H), 7.23 (m, 3H), 7.17 (m, 3H), 4.86 (s, 2H), 2.58 (s, 3H), 1.45 (br s, 9H)

Mass (M+H$^+$) calcd for $C_{27}H_{26}FN_7O_2$ 499.2, found 500.2.

Step 5: Preparation of N-((5-([1,2,4]triazolo[1,5-a]pyridin-6-yl)-4-(6-methylpyridin-2-yl)-1H-imidazol-2-yl)methyl)-2-fluoroaniline (Compound 1a)

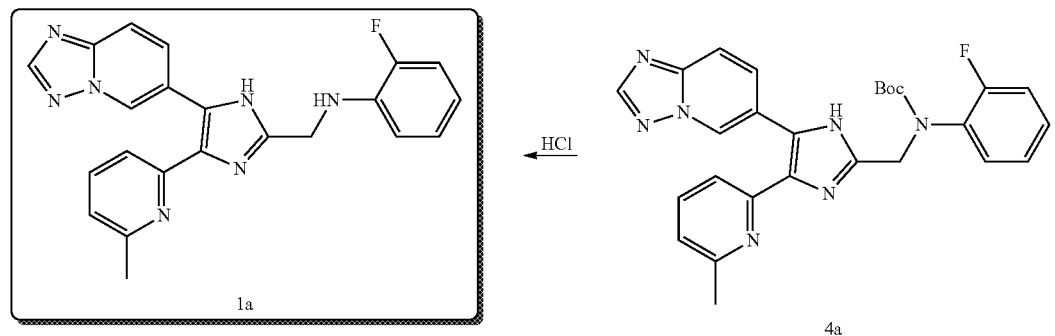

CH$_2$Cl$_2$/EtOAc/MeOH was applicable as the reaction solvent used in the synthesis of Compound 1a.

TABLE 4

| Type of solvent | Type of acid | Reaction time | Compound 4a | Compound 1a |
|---|---|---|---|---|
| CH$_2$Cl$_2$ | HCl | 1 h | 1.1% | 98.4% |
| EtOAc | HCl | 1 h | 37.8% | 62.2% |
| MeOH | HCl | 1 h | 92.8% | 6.8% |
| CH$_2$Cl$_2$ | HCl | 3 h | 0.0% | 98.6% |
| EtOAc | HCl | 3 h | 7.2% | 92.2% |
| MeOH | HCl | 3 h | 64.0% | 35.7% |

CH$_2$Cl$_2$ (dichloromethane) was selected as a solvent in consideration of the yield and the ease of subsequent concentration removal of the solvent.

Preferred synthesis examples according to the above results are as follows.

After tert-butyl (5-([1,2,4]triazolo[1,5-a]pyridin-6-yl)-4-(6-methylpyridin-2-yl)-1H-imidazol-2-yl)methyl(2-fluorophenyl)carbamate (98 mg, 0.196 mmol) was put into dichloromethane and the resulting mixture was stirred, hydrochloric acid (4 M in dioxane, 0.49 ml, 1.96 mmol) was slowly added thereto to perform a reaction at room temperature for 2 hours. After the reaction was completed, the resulting product was washed with a saturated aqueous sodium hydrogen carbonate solution and extracted with dichloromethane. The solvent of the extract was removed under reduced pressure to obtain 71 mg of a target product N-((5-([1,2,4]triazolo[1,5-a]pyridin-6-yl)-4-(6-methylpyridin-2-yl)-1H-imidazol-2-yl)methyl)-2-fluoroaniline in a yield of 91%.

$^1$H NMR (CDCl3, 400 MHz) δ8.96 (br s, 1H), 8.38 (s, 1H), 7.76-7.83 (m, 2H), 7.45 (t, 1H), 7.22 (d, 1H), 6.97-7.00 (m, 3H), 6.75 (m, 2H), 4.58 (m, 1H), 4.54 (s, 2H), 2.42 (s, 3H)

Mass (M+H$^+$) calcd for $C_{22}H_{18}FN_7$ 399.2, found 400.3.

Example 2: Preparation of 2-([1,2,4]triazolo[1,5-a]pyridin-6-yl)-2-bromo-1-(6-methylpyridin-2-yl)ethanone bromate (Compound 2a)(Step A)

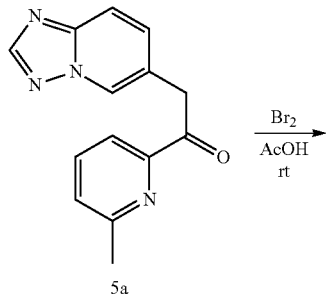

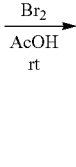

After 2-([1,2,4]triazolo[1,5-a]pyridin-6-yl)-1-(6-methylpyridin-2-yl)ethanone (2.47 g, 9.79 mmol) was put into acetic acid and the resulting mixture was stirred, a bromine solution (1.57 g, 9.79 mmol, in acetic acid) was added thereto to perform a reaction at room temperature for 1 hour. After the reaction was completed, the solvent was removed under reduced pressure. The solvent-free mixture was washed with methyl butyl ether and dried to obtain 2.66 g of a target compound 2-([1,2,4]triazolo[1,5-a]pyridin-6-yl)-2-bromo-1-(6-methylpyridin-2-yl)ethanone bromate in a yield of 66%.

$^1$H NMR (DMSO, 400 MHz) δ8.66 (d, 2H), 7.90 (m, 2H), 7.60 (m, 2H), 7.37 (s, 1H), 6.69 (s, 1H), 2.61 (d, 3H)

The preparation method according to the present invention can not only allow inexpensive and safe reagents to be used, but also simplify the synthesis steps and purification methods to improve the reaction yield, thereby maximizing the production efficiency of a TGF-β inhibitor represented by Chemical Formula 1 to be used usefully for mass production.

What is claimed is:

1. A method for preparing a compound of Chemical Formula 1, the method comprising: obtaining a compound of Chemical Formula 4 by reacting a compound of Chemical Formula 2 with a compound of Chemical Formula 3, and
obtaining a compound of Chemical Formula 1 by deprotecting the compound of Chemical Formula 4:

[Chemical Formula 2]

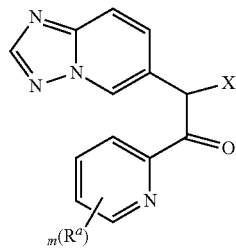

[Chemical Formula 3]

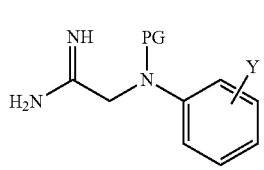

[Chemical Formula 4]

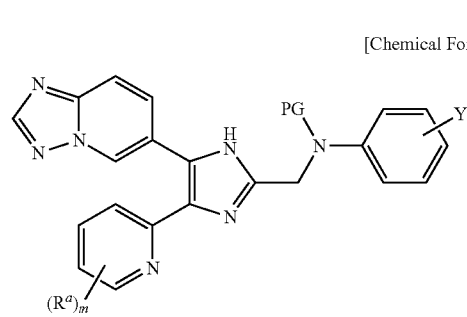

[Chemical Formula 1]

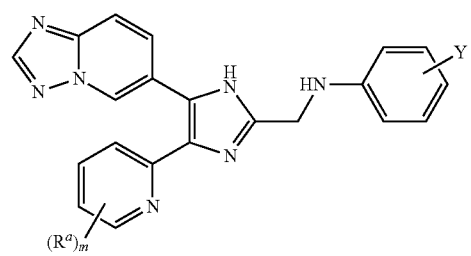

wherein, in the formulae,

X and Y are each independently halogen;

PG is a protecting group selected from the group consisting of butoxycarbonyl (Boc), benzyloxycarbonyl (Cbz), 9-fluorenylmethoxycarbonyl (Fmoc), acetyl, benzoyl and tosyl;

$R^a$ is independently hydrogen, halogen, C1-6 alkyl, C1-6 haloalkyl, C3-6 cycloalkyl, hydroxyl, —O-C1-6 alkyl, —O-C1-6 haloalkyl, —O-C3-6 cycloalkyl, amino, —NH-C1-6 alkyl, —NH-C1-6 haloalkyl, —NH-C3-6 cycloalkyl, —S-C1-6 alkyl, —S-C1-6 haloalkyl, —S-C3-6 cycloalkyl, cyano, or nitro; and m is 0, 1, 2, 3 or 4.

2. The method of claim 1, wherein the compound of Chemical Formula 1 is a compound of Chemical Formula 1a:

[Chemical Formula 1a]

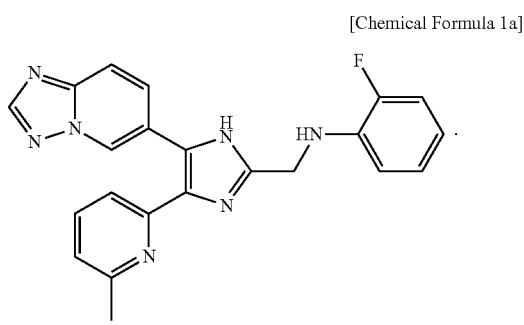 [SMILES: Cc1cccc(-c2nc(CNc3ccccc3F)[nH]c2-c2ccc3ncnn3c2)n1]

3. The method of claim 1, wherein the compound of Chemical Formula 2 is a compound of Chemical Formula 2a:

[Chemcial Formula 2a]

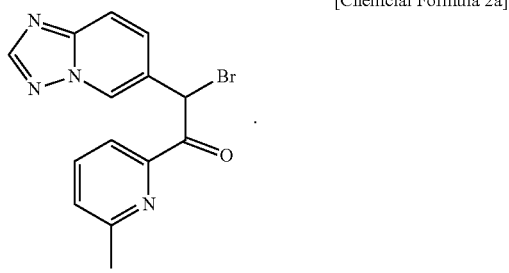

4. The method of claim 1, wherein the compound of Chemical Formula 3 is a compound of Chemical Formula 3a:

[Chemical Formula 3a]

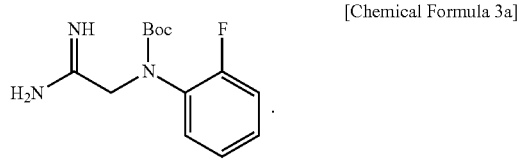 [SMILES: CC(C)(C)OC(=O)N(CC(=N)N)c1ccccc1F]

5. The method of claim 1, wherein the compound of Chemical Formula 4 is a compound of Chemical Formula 4a:

[Chemical Formula 4a]

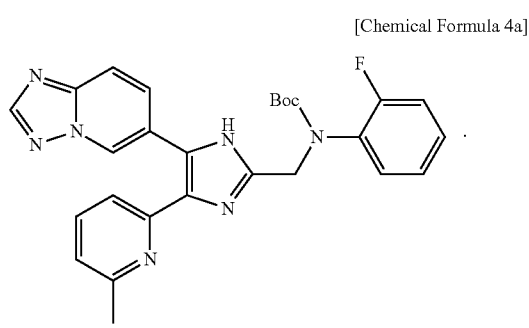 [SMILES: Cc1cccc(-c2nc(CN(C(=O)OC(C)(C)C)c3ccccc3F)[nH]c2-c2ccc3ncnn3c2)n1]

6. The method of claim 1, wherein the obtaining of the compound of Chemical Formula 4 by reacting the compound of Chemical Formula 2 with the compound of Chemical Formula 3 comprises coupling an amine of the compound of Chemical Formula 3 to a position of an X substituent of the compound of Chemical Formula 2 in the presence of a base, and then forming imidazole by a dehydration reaction.

7. The method of claim 6, wherein the base is selected from the group consisting of potassium bicarbonate, potassium carbonate, potassium phosphate, sodium acetate, 1,4-diazabicyclo[2.2.2]octane (DABCO), and triethylamine.

8. The method of claim 6, wherein in the reaction, dimethylformamide (N,N-dimethylformamide, DMF), acetonitrile, tetrahydrofuran (THF), toluene or a mixture thereof is used as a reaction solvent.

9. The method of claim 6, wherein the reaction further comprises a desiccant to prevent side reactions, and the desiccant is selected from among molecular sieves, sodium sulfate and magnesium sulfate.

10. The method of claim 6, wherein the reaction is performed at 20° C. to 95° C.

11. The method of claim 1, wherein in the obtaining of the compound of Chemical Formula 1 by deprotecting the compound of Chemical Formula 4, dichloromethane, ethylacetate, methanol or a mixture thereof is used as a reaction solvent.

12. The method of claim 1, wherein the compound of Chemical Formula 2 is obtained by converting an $R^b$ substituent of a compound of Chemical Formula 5 into halogen,

[Chemcial Formula 5]

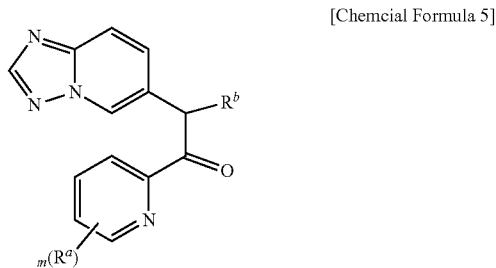

in the formula, $R^a$ is independently hydrogen, halogen, C1-6 alkyl, C1-6 haloalkyl, C3-6 cycloalkyl, hydroxyl, —O-C1-6 alkyl, —O-C1-6 haloalkyl, —O-C3-6 cycloalkyl, amino, —NH-C1-6 alkyl, —NH-C1-6 haloalkyl, —NH-C3-6 cycloalkyl, —S-C1-6 alkyl, —S-C1-6 haloalkyl, —S-C3-6 cycloalkyl, cyano, or nitro;

m is 0, 1, 2, 3 or 4; and $R^b$ is hydrogen, hydroxyl, cyano, nitro, or amino.

13. The method of claim 12, wherein the compound of Chemical Formula 5 is a compound of Chemical Formula 5a:

[Chemcial Formula 5a]

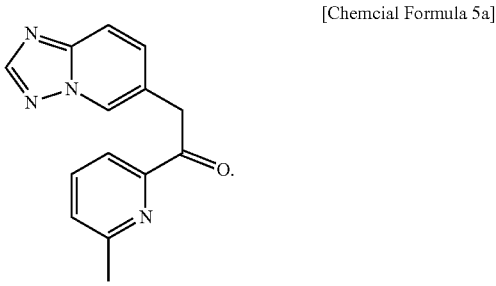 [SMILES: Cc1cccc(C(=O)Cc2ccc3ncnn3c2)n1]

14. The method of claim 1, wherein the compound of Chemical Formula 3 is obtained by forming an amidine through a Pinner reaction of a nitrile in Chemical Formula 6,

[Chemical Formula 6]

in the formula,
Y is halogen; and
PG is a protecting group selected from the group consisting of butoxycarbonyl (Boc), benzyloxycarbonyl (Cbz), 9-fluorenylmethoxycarbonyl (Fmoc), acetyl, benzoyl and tosyl.

15. The method of claim 14, wherein the Pinner reaction comprises forming an iminoester salt by reacting the compound of Chemical Formula 6 with an alkoxy, and obtaining a compound of Chemical Formula 3 by reacting the iminoester salt with an ammonium salt.

16. The method of claim 14, wherein the compound of Chemical Formula 6 is obtained by introducing a protecting group into an amine of a compound of Chemical Formula 7,

[Chemical Formula 7]

in the formula,
Y is a halogen.

17. The method of claim 16, wherein the compound of Chemical Formula 7 is obtained by introducing acetonitrile into an amine of a compound of Chemical Formula 8 in the presence of a base,

[Chemical Formula 8]

in the formula,
Y is halogen.

18. A compound represented by Chemical Formula 4:

[Chemical Formula 4]

in the formula,
Y is halogen;
PG is a protecting group selected from the group consisting of butoxycarbonyl (Boc), benzyloxycarbonyl (Cbz), 9-fluorenylmethoxycarbonyl (Fmoc), acetyl, benzoyl and tosyl;
$R^a$ is independently hydrogen, halogen, C1-6 alkyl, C1-6 haloalkyl, C3-6 cycloalkyl, hydroxyl, —O-C1-6 alkyl, —O-C1-6 haloalkyl, —O-C3-6 cycloalkyl, amino, —NH-C1-6 alkyl, —NH-C1-6 haloalkyl, —NH-C3-6 cycloalkyl, —S-C1-6 alkyl, —S-C1-6 haloalkyl, —S-C3-6 cycloalkyl, cyano, or nitro; and
m is 0, 1, 2, 3 or 4.

19. The compound of claim 18, wherein the compound is represented by Chemical Formula 4a:

[Chemical Formula 4a]

* * * * *